(12) United States Patent
Smith et al.

(10) Patent No.: US 6,194,562 B1
(45) Date of Patent: Feb. 27, 2001

(54) ENDOTOXIN REDUCTION IN NUCLEIC ACID PURIFICATION

(75) Inventors: Craig E. Smith, Oregon; Donald A. Creswell, Cottage Grove; Rex M. Bitner, Cedarburg; Douglas H. White; Braeden L. Butler, both of Madison; Scott A. Lesley, Oregon, all of WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 09/064,449

(22) Filed: Apr. 22, 1998

(51) Int. Cl.$^7$ .................... C07H 21/00; C07H 21/02; C07H 21/04; C12N 15/00; C12N 15/09

(52) U.S. Cl. .................. 536/24.5; 536/25.41; 536/25.42; 435/320.1; 935/77

(58) Field of Search ................ 536/25.4, 25.41, 536/25.42; 435/6, 320.1; 935/76, 77, 78

(56) References Cited

U.S. PATENT DOCUMENTS

| | | |
|---|---|---|
| 3,897,309 | 7/1975 | Grabner . |
| 4,059,512 | 11/1977 | Harris . |
| 4,491,660 | 1/1985 | Gendrich et al. . |
| 4,661,260 | 4/1987 | Kodama et al. . |
| 4,808,314 | 2/1989 | Karplue et al. . |
| 4,866,034 | * 9/1989 | Ribi .......................................... 514/2 |
| 4,885,168 | 12/1989 | Hashimoto et al. . |
| 5,059,527 | 10/1991 | White et al. . |
| 5,169,535 | 12/1992 | Adachi et al. . |
| 5,346,994 | 9/1994 | Chomczynski . |
| 5,403,917 | 4/1995 | Boos et al. . |

(List continued on next page.)

FOREIGN PATENT DOCUMENTS

| | | |
|---|---|---|
| 2223821 | 6/1996 | (CA) . |
| WO 95/06652 | 3/1995 | (WO) . |
| WO 95/21177 | 8/1995 | (WO) . |
| WO 96/41811 | 12/1996 | (WO) . |
| WO97/32893 | * 9/1997 | (WO) . |

OTHER PUBLICATIONS

Aida et al., "Removal of endotoxin from protein solutions by phase separation using Triton X–114" *Journal of Immunological Methods* 132:191–195, 1990.
Anspach et al., "Removal of endotoxins by affinity sorbents" *Journal of Chromatography A*. 711:81–92 (1995).
Cotten et al., "Lipopolysaccharide is a frequent contaminant of plasmid DNA preparations and can be toxic to primary human cells in the presence of adenovirus" *Gene Therapy* 1:239–246 (1994).
Davis et al."Direct Gene Transfer into Skeletal muscle In Vivo: Factors Affecting Efficiency of Transfer and Stability of Expression" *Human Gene Therapy* 4:151–159 (1993).
Karplus et al., "A new method for reduction of endotoxin contamination from protein solutions" *Journal of Immunological Methods* 105:211–220 (1987).
Kurt–Othmer Encyclopedia of Chemical Technology, vol. 21, 4th ed., Mary Howe–Grant, ed., John Wiley & Sons, pub 1991, pp. 1020–1023.
Manthorpe, et al., "Gene Therapy by Intramuscular Injection of Plasmid DNA: Studies on Firefly Luciferase Gene Expression in Mice" *Human Gene Therapy* 4:419–431 (1993).
Marvin et al., "Release of Outer Membrane Fragments from Wild–Type *Escherichia coli* and from Several *E. coli* Lipopolysaccharide Mutants by EDTA and Heat Shock Treatments" *Journal of Bacteriology* 171(10):5262–5267 (1989).
MØlvig et al., "Removal of Endotoxin from Culture Media by a Polymyxin B Sepharose Column", *Scand. J. Immunol.* 26:611–619, (1987).
Montibrand, et al "Improved method for the removal of endotoxin from DNA" *Journal of Biotechnology* 44:43–46 (1996).
Morrison, et al. "Endotoxin and Disease Mechanisms", *Ann. Rev. Med.*, 38:417–432 1987.
PerSeptive Diagnotics Product Guide for BioMag®MINI–PREP DNA Purification Kit (Catalog No. 8–MB4008K)4 pages Feb. 27, 1995.
Promega Corporation, 1998 Product Catalog, cover, pp. 182–183, and 199–200.
QIAGEN Plasmid Purification Handbook, Jan. 1997.
Shigui et al., "Removal of Endotoxin from Recombinant Protein Preparations" *Clinical Biochemistry*, 30(6):455–463, (1997).
Sigma–Aldrich 1997 Catalog, cover and p. 448.
Weber et al., "Effects of Lipopolysaccharide on Transfection Efficiency in Eukaryotic Cells", *Biotechniques* 19(6):930–940 (Dec. 1995).
Wicks et al., "Bacterial Lipopolysaccharide Copurifies with Plasmid DNA: Implications for Animal Models and Human Gene Therapy", *Human Gene Therapy* 6:317–323 (Mar. 1995).

*Primary Examiner*—Ethan Whisenant
(74) *Attorney, Agent, or Firm*—Michael Best & Friedrich LLP; Grady J. Frenchick; Karen B. King

(57) ABSTRACT

The present invention presents a novel method for removing endotoxins from nucleic acids, such as DNA, RNA, or hybrids thereof, contaminated therewith. Nucleic acid solutions which can be treated using the method of this invention include, but are not limited to, lysates of gram-negative bacteria and nucleic acid solutions contaminated with endotoxins from external sources. The present method removes endotoxins from such solutions using silica-based materials, such as silica gel particles, magnetic silica particles, or diatomaceous earth. In a preferred aspect of the method of this invention, magnetic silica particles are used to isolate plasmid DNA from a lysate of gram-negative bacteria transformed with the plasmid DNA. Application of the disclosed method produces nucleic acids which are sufficiently free of endotoxin contamination to be useful for a variety of different practical applications.

30 Claims, 4 Drawing Sheets

U.S. PATENT DOCUMENTS

| | | |
|---|---|---|
| 5,561,064 * | 10/1996 | Marquet et al. .................. 435/320.1 |
| 5,576,185 | 11/1996 | Coulter et al. . |
| 5,589,459 | 12/1996 | Porro . |
| 5,591,628 | 1/1997 | Baek et al. . |
| 5,674,997 | 10/1997 | Woodard et al. . |
| 5,693,785 | 12/1997 | Woodard et al. . |
| 5,747,663 * | 5/1998 | Colpan et al. ...................... 536/25.4 |
| 5,945,525 * | 8/1999 | Uematsu et al. .................. 536/25.42 |
| 5,981,235 * | 11/1999 | Shultz et al. ........................ 435/91.1 |
| 5,990,301 * | 11/1999 | Colpan et al. ...................... 536/25.4 |

* cited by examiner

DE Endotoxin Binding Curve

ENDOTOXIN REDUCTION IN NUCLEIC ACID PURIFICATION

CROSS-REFERENCE TO RELATED APPLICATIONS

Not Applicable

STATEMENT REGARDING FEDERALLY SPONSORED RESEARCH OR DEVELOPMENT

Not Applicable

TECHNICAL FIELD

This invention relates generally to methods for selectively reducing the concentration of endotoxins from a solution containing endotoxins and nucleic acids, such as a solution derived from the disruption of gram-negative bacteria or a solution of nucleic acids contaminated with endotoxins from the environment. This invention also relates to methods for isolating nucleic acids, such as plasmid DNA, chromosomal DNA, total RNA, mRNA, or RNA/DNA hybrids using a silica matrix.

BACKGROUND

Generally speaking, an endotoxin is a lipopolysaccharide material found in the cell wall of most gram-negative bacilli, including *Escherichia coli*. During lysis of bacterial cell, such as is done to release plasmids from *E coli* transformants, endotoxins are released into the lysate produced thereby. Endotoxin contamination in a nucleic acid sample can adversely limit the utility of the sample, particularly in applications which are sensitive to such contamination. For example, the transfection efficiency of several different cultured eukaryotic cell lines, including HeLa, Huh7, COS7, and LMH, have been shown to be sharply reduced in the presence of endotoxins. Weber, M. et al. 1995, *BioTechniques* 19(6):930–939. Endotoxins have also been found to be toxic to primary human cells, such as primary human skin fibroblasts and primary human melanoma cells, in the presence of entry-competent adenovirus particles. Cotten, M. et al. 1994, *Gene Therapy* 1:239–246. Endotoxins have also been shown to produce striking pathophysiological reactions when introduced into animals, including high fever, vasodilation, diarrhea and, in extreme cases, fatal shock. Morrison, David C. 1987, *Ann Rev. Med.* 38:417–32.

Endotoxins are not readily separated from nucleic acids, particularly from plasmid DNA. *QIAGEN Plasmid Purification Handbook* (January 1997), p. 55 (hereinafter, the "Handbook"). Endotoxins tend to form mycellar structures which have a similar density, size, and charge distribution on the outer surface of the mycells Id.. As a result, endotoxins co-purify with nucleic acids, particularly with plasmid DNA, in most nucleic acid isolation procedures used today. For example, endotoxins appear in the same band as the DNA-ethidium bromide complex in the cesium chloride gradients used to separate plasmid DNA from other materials in a bacteria lysate Id. and Cotten et al., supra. Endotoxins also co-migrate and co-elute with plasmid DNA from size exclusion and from anion exchange resins. *Handbook*, p. 55.

Phase separation with Triton X-114 has been used to reduce endotoxin levels in solutions of plasmid DNA. However removal of endotoxins with Triton X-114 requires multiple, labor-intensive, phase separation steps, with some plasmid DNA lost in each extraction step. Shigui L. et al. *Clinical Biochemistry* 1997, 30(6): 455–463. Various groups of researchers have obtained mixed results with Triton X-114 extraction, with some obtaining unsatisfactory endotoxin removal from plasmid DNA solutions. See, e.g. Montbriand, P. M. et al. 1996 *J. Biotechnol* 44:43–46; Manthorpe, M et al. 1993, *Hum. Gene Ther.* 4: 419–431.

Affinity sorbents have also been developed for the removal of endotoxins from protein or DNA solutions. See, e.g. Anspach, F. B. et al. 1995 *J. Chromatography* 711:81–92 [protein purification]; Montbriand, supra, p. 44 [DNA purification]. For example, polymyxin B, a cationic polypeptide which stoichiometrically binds to a portion of the LPS molecule, has been linked to various resins, such as Sepharose or agarose, and used to remove endotoxins from a solution of DNA. Molvig, J. and Baek, L. (1987) *Immunochemistry* 26:611–619 [Sepharose resin]; Montbriand, supra at 44 [agarose resin]. Affinity resins are generally difficult to synthesize and costly to purchase. Affinity resins also present problems not presented by any of the other, traditional, methods of nucleic acid isolation and/or endotoxin removal described briefly above.

One research group, Montbriand et al., conducted a study of the effectiveness of various types of affinity resins and resin formats in the removal of endotoxins from plasmid DNA. Montbriand, supra. That group removed endotoxins from solutions of plasmid DNA with a polymyxin B-sepharose affinity resin, using gravity flow chromatography, spin column chromatography, and bulk chromatography. Montbriand et al. reported that bulk chromatography resulted in the most efficient purification of DNA, but polymyxin B release into the DNA solution purified therewith was problematic in some applications, such as in-vivo administration of purified DNA to humans. Montbriand et al. obtained some plasmid DNA which were relatively free of endotoxins, using polymyxin-agarose resins. But, all three techniques used by that research group to purify DNA with the resins resulted in a significant loss of DNA.

Some molecular biology companies have developed kits for use in isolating plasmid DNA for transformation of eukaryotic cells, under conditions where endotoxins are digested and separated from the DNA. One such kit is the "EndoFree Plasmid Maxi Kit" sold by QIAGEN, Inc. (Santa Clarita, Calif.) Instructions for use of that kit and detailed descriptions of all but one of the solutions provided for use with that kit are provided the *QIAGEN Plasmid Purification Handbook*. The only solution whose composition is not described in the Handbook is "Buffer ER". The Handbook also fails to provide any information about the composition of the material in the "QIA-tip" used to bind DNA after Buffer ER is used to "remove endotoxins" from the lysate solution filtered according to the isolation procedure described therein. The DNA isolation procedure described in EndoFree Plasmid Maxi Kit portion of the *Handbook* involves multiple steps many of which result in a loss of plasmid DNA.

A group of researchers, Wicks et al., recently compared use of a QIAGEN plasmid DNA kit with a lysozyme digestion step to a similar kit which did not include any enzymes or other materials designed to remove endotoxins. Wicks, I. P. et al. (March 1995) *Human Gene Therapy* 6:317–323, at p. 319. They found endotoxins in the range of 50–500 µg/ml in plasmid DNA isolated using the kit with a lysozyme treatment step, and endotoxin concentrations of over 3 mg/ml using kits with no such digestion step. Id. Wicks et al. also note, however, that use of both plasmid DNA isolation procedures resulted in a significant loss in the amount of DNA isolated, compared to a considerably more complex procedure described therein. Specifically, Wicks et al. described a plasmid DNA and endotoxin removal procedure, wherein plasmid DNA was isolated from spheroplasts, and wherein endotoxins where removed from the DNA isolated from the spheroplasts, using polymyxin B-agarose chromatography. Id. at 318–20.

Note, incidentally, that the QIAGEN EndoFree Plasmid Maxi kit is designed solely for plasmid DNA isolation. The alkaline lysis step in the first part of the procedure inherently degrades any RNA molecules present in the bacteria cells. The neutralization and filtration steps are expressly designed to precipitate and remove chromosomal DNA. in short, the QIAGEN kit is clearly not suited for the isolation of any species of nucleic acid other than plasmid DNA.

The present invention addresses the need for methods and materials for treating solutions of nucleic acids containing endotoxins to reduce the concentration of endotoxins contained therein. The invention described herein below offers a rapid and efficient means for removing endonucleases from such solutions, thereby providing purified nucleic acids which can be used in a variety of biological applications, including transfection of cultured cells and in vivo administration of nucleic acids to organisms which are susceptible to sepsis.

BRIEF SUMMARY OF THE INVENTION

The method of this invention uses a first silica matrix and a second silica matrix, each of which comprise silica, preferably in the form of silica gel, sileous oxide, solid silica such as glass or diatomaceous earth, or a mixture of two or more of the above. The first silica matrix is preferably in a form which, under the conditions of use set forth herein below, will form a complex with endotoxins, but which will not form a complex with the target nucleic acid in the presence of a solution of the target nucleic acid which is substantially free of chaotropic agents. The second silica matrix can be in any form which will form a complex with the target nucleic acid, under the conditions of use set forth herein below, provided the target nucleic acid can be separated from the complex upon addition of an elution solution.

Briefly, in one aspect, the present invention is a method of reducing the concentration of endotoxins in a first solution comprising a target nucleic acid and endotoxins, the method comprising: (a) providing a first silica matrix equilibrated with a first equilibration buffer which is substantially free of chaotropic agents; (b) providing the first solution, wherein the first solution is substantially free of chaotropic agents; (c) combining the first silica matrix and first solution, wherein at least one of the endotoxins forms an endotoxin/matrix complex with the first silica matrix, thereby producing a second solution containing fewer endotoxins than the first solution; and (d) separating the second solution from the endotoxin/matrix complex.

The target nucleic acid isolated in accordance with the method of this invention can be any nucleic acid, such as any type of RNA, DNA, or RNA/DNA hybrid. The nucleic acid can be, for example, plasmid DNA, DNA fragments produced from restriction enzyme digestion, amplified DNA produced by an amplification reaction such as the polymerase chain reaction (PCR), single-stranded DNA, mRNA, or total RNA. The present method is most preferably used to remove endotoxin from plasmid DNA isolated from genetically transformed gram-negative bacteria, as endotoxin contamination in such nucleic acid solutions is historically the most problematic. However, the present method can be used to remove endotoxins from any one of a number of other nucleic acid samples.

In a preferred practice of the invention, the target nucleic acid is further isolated from other materials in the second solution after it is separated from the first silica matrix and the endotoxin/matrix complex in step (d) by the additional steps comprising: (e) combining the solution with a second silica matrix in the presence of a binding agent, thereby forming a nucleic acid/matrix complex between the target nucleic acid and the second silica matrix; (f) separating the second silica matrix from the solution; and (g) eluting the target nucleic acid from the nucleic acid/matrix complex.

The present invention provides a convenient and efficient means for reducing the concentration of endotoxins in a solution of any nucleic acid material, including plasmid DNA. This invention enables one to reduce the concentration of endotoxins in a nucleic acid solution by forming a complex between endotoxins in the solution and a silica matrix, under conditions where the endotoxin preferably binds to the matrix, leaving the nucleic acid in solution to be further isolated, if so desired. The present method requires no multiple extraction steps, like the Triton X-114 extraction methods, no time-consuming protease digestion steps, and no expensive affinity chromatography resins. Inexpensive silica matrices suitable for use in practicing the method of the present invention are also commercially available, such as the Wizard® Minipreps DNA Purification Resin (cat. no. A7141), Wizard® Plus SV Minipreps DNA purification System (cat. no.'s A1330, 1340, 1460, or 1470), MagneSil™ magnetic particles (cat. nos. A2132 and A2132), all available from Promega Corp.,( Madison, Wis.); and the BioMag® DNA Sep magnetic particles available from PerSeptive Diagnostics.

The nucleic acids purified using the method of the present invention are sufficiently free of endotoxins for additional processing, analysis, or even administration to mammals. Applications of the present method to reduce endotoxins from a variety of different media will become apparent from the detailed description of the invention below. Those skilled in the art of this invention will appreciate that the detailed description of the invention, below, is meant to be exemplary only and should not be viewed as limiting the scope of the invention.

DETAILED DESCRIPTION OF THE INVENTION

Figure 1:
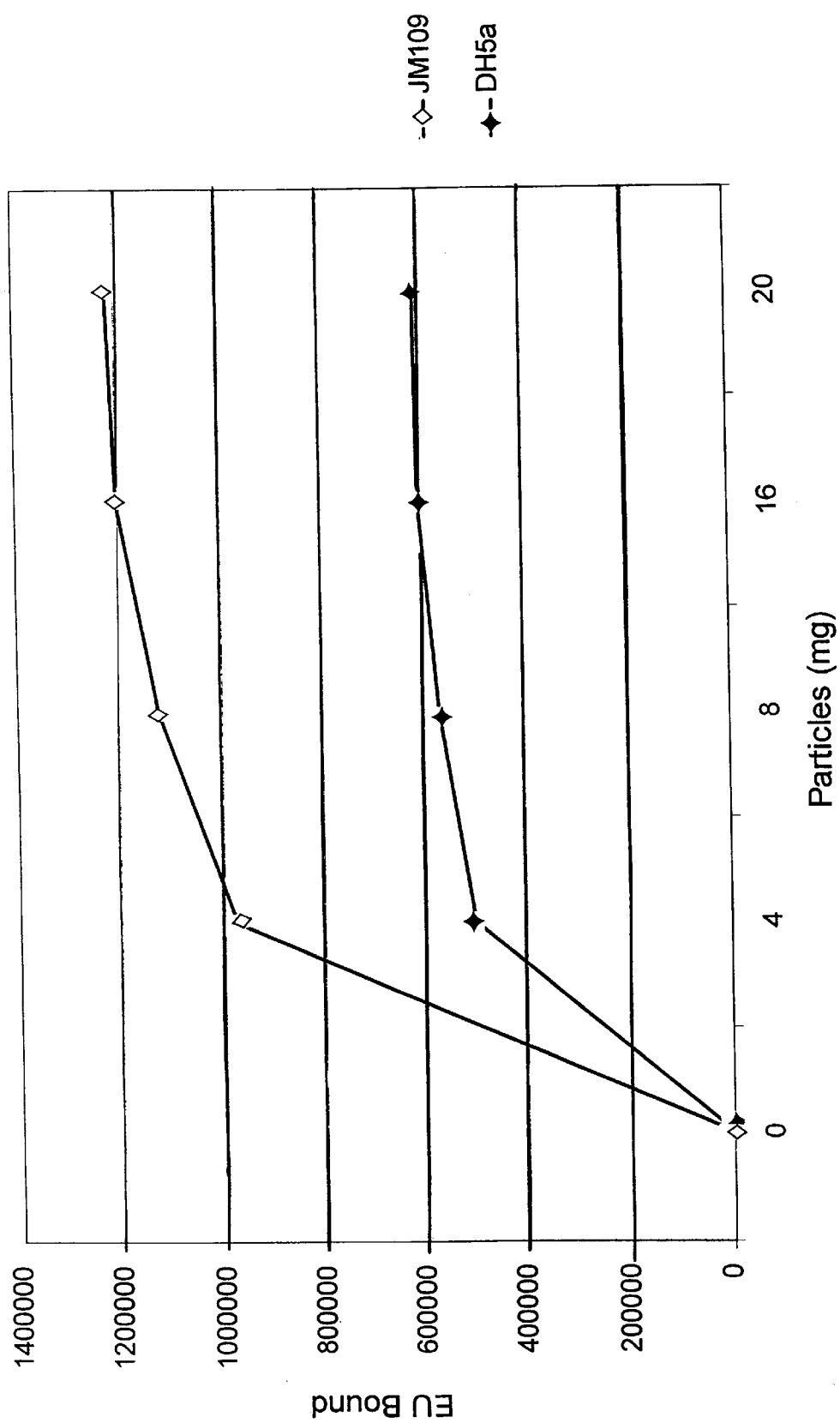
FIG. 1 is a plot of units of endotoxin bound vs the number of milligrams of particles added to lysates of each of two different strains of E coli bacteria, JM109 (◇) or DH5α (◆).

Each silica matrix used in the present invention is also preferably in a form which can be removed from a nucleic acid solution after combination therewith, by application of an external force. When the silica matrix is in a non-magnetic form, such as silica gel particles, ground glass, controlled pore glass particles, a resin, diatomaceous earth, a silica filter, or a filter embedded with embedded with silica particles, the silica matrix can be separated from the nucleic acid solution using gravity, centrifugation, or vacuum filtration. When the silica matrix is magnetic, such as a silica magnetic particle, it can be removed using a magnetic force or using any of the methods used to remove non-magnetic silica matrices cited above. Resins particularly preferred for use as the first or second silica matrix in the present invention include resins described in PCT Publication Number WO 95/06652, incorporated herein by reference, resins sold by Promega Corporation for use in plasmid DNA isolation, i.e. Wizard® Minipreps DNA Purification Resins. Magnetic silica matrices particularly preferred for use as the first or second silica matrix in the present invention include MagneSil™ paramagnetic particles available from Promega, BioMag® DNA Sep magnetic particles available from Per-Septive Diagnostics, and the magnetic silica particles described in PCT International Patent Application No. PCT/US98/01149, published on Jul. 23, 1998, as Publication Number WO 9831890 for an invention titled: METHODS OF ISOLATING BIOLOGICAL TARGET MATERIALS USING SILICA MAGNETIC PARTICLES, incorporated by reference herein.

When the silica matrix is magnetic, it is preferably a magnetic silica particle. A magnetic silica particle can be separated from a solution using any of the external means described above for use with other silica matrices. But, the external means used to separate a magnetic silica particle from a solution is preferably magnetic force. The first silica matrix and second silica matrix are preferably both magnetic silica particles.

The term "silica gel" as used herein refers to chromatography grade silica gel, a substance which is commercially available from a number of different sources. Silica gel is most commonly prepared by acidifying a solution containing silicate, e.g. sodium silicate, to a pH of less than 10 or 11 and then allowing the acidified solution to gel. See, e.g. silica preparation discussion in *Kurt-Othmer Encyclopedia of Chemical Technology*, Vol. 6, 4th ed., Mary Howe-Grant, ed., John Wiley & Sons, pub., 1993, pp. 773–775.

The term "glass particles" as used herein means particles of crystalline silicas (e.g., α-quartz, vitreous silica), even though crystalline silicas are not formally "glasses" because they are not amorphous, or particles of glass made primarily of silica.

As used herein, the term "magnetic silica particles" refers to silica matrices which are further comprised of materials which have no magnetic field but which form a magnetic dipole when exposed to a magnetic field, i.e., materials capable of being magnetized in the presence of a magnetic field but which are not themselves magnetic in the absence of such a field. The term "magnetic" as used in this context includes materials which are paramagnetic or super paramagnetic materials. The term "magnetic", as used herein, also encompasses temporarily magnetic materials, such as ferromagnetic or ferrimagnetic materials.

When either the first or second silica matrix is a silica magnetic particle, the size of the particle is preferably selected as follows. Smaller magnetic silica particles provide more surface area (one per weight unit basis) for adsorption, but smaller particles are limited in the amount of magnetic material which can be incorporated into such particles compared to larger particles. The median particle size of the magnetic silica particles used in a particularly preferred embodiment of the present invention is about 1 to 15 μm, more preferably about 3 to 10 μm, and most preferably about 4 to 7 μm. The particle size distribution may also be varied. However, a relatively narrow monodal particle size distribution is preferred. The monodal particle size distribution is preferably such that about 80% by weight of the particles are within a 10 μm range about the median particle size, more preferably within an 8 μm range, and most preferably within a 6 μm range.

The silica magnetic particle or any other silica particle used in the present invention preferably has pores which are accessible from the exterior of the particle. The pores are preferably of a controlled size range sufficiently large to admit the target material, i.e. endotoxins in the case of the first silica matrix or the target nucleic acid in the second silica matrix, into the interior of the particle and to bind to the silica gel material on the interior surface of most such pores. The pores of the most preferred form of the magnetic silica particles are designed to provide a large surface area of silica gel material capable of binding a biological target material, particularly a nucleic material and/or an endotoxin. The total pore volume of a silica magnetic particle, as measured by nitrogen BET method, is preferably at least about 0.2 ml/g of particle mass. Of the total pore volume measured by nitrogen BET, preferably at least about 50% of the pore volume is contained in pores having a diameter of 600 Å or greater.

The magnetic silica particles may contain substances, such as transition metals or volatile organics, which could adversely affect the utility of nucleic acids substantially contaminated with such substances. Specifically, such contaminants could affect downstream processing, analysis, and/or use of the such materials, for example, by inhibiting enzyme activity or nicking or degrading the nucleic acids isolated therewith. Any such substances present in the magnetic silica particles used in the present invention are preferably present in a form which does not readily leach out of the particle and into the isolated biological target material produced according to the methods of the present invention. Iron is one such undesirable contaminant, particularly when the biological target material is a nucleic acid.

Iron, in the form of magnetite, is present at the core of a particularly preferred form of the magnetic silica particles of the present invention, i.e. the SOCM particles. Iron has a broad absorption peak between 260 and 270 nanometers (nm). Nucleic acids have a peak absorption at about 260 nm, so iron contamination in a nucleic acid sample can adversely affect the accuracy of the results of quantitative spectrophotometric analysis of such samples. Any iron containing magnetic silica particles used to isolate nucleic acids using the present invention preferably do not produce isolated nucleic acid material sufficiently contaminated with iron for the iron to interfere with spectrophotometric analysis of the material at or around 260 nm.

The most preferred magnetic silica particles used in the methods of the present invention, leach no more than 50 ppm, more preferably no more than 10 ppm, and most preferably no more than 5 ppm of transition metals when assayed as follows. Specifically, 0.33 g of the particles (oven dried @ 110° C.) into 20 ml. of 1 N HCl aqueous solution (using demonize water). The resulting mixture is then agitated only to disperse the particles. After about 15 minutes total contact time, a portion of the liquid from the mixture is then analyzed for metals content. Any conventional elemental analysis technique may be employed to quantify the amount of transition metal in the resulting liquid, but inductively coupled plasma spectroscopy (ICP) is preferred.

At least two commercial magnetic silica particles are particularly preferred for use as the first or second silica matrices in the present invention, the MagneSil™ magnetic silica particles commercially available from Promega Corporation and the BioMag® Magnetic Particles available from PerSeptive Biosystems. Any source of magnetic force sufficiently strong to separate the magnetic silica particles from a solution would be suitable for use in the present invention. However, the magnetic force is preferably provided in the form of a magnetic separation stand, such as one of the MagneSphere® Technology Magnetic Separation Stands (cat. no.'s Z5331 to 3, or Z5341 to 3) from Promega Corporation.

The first silica matrix provided in step (a) of the invention and the first solution provided in step (b) must each be substantially free of chaotropic agents. First silica matrix provided in step (a) is equilibrated with a first equilibration buffer which must be, similarly, substantially free of chaotropic agents. The term "chaotropic agent" as used herein refers to salts of particular ions which, when present in a sufficiently high concentration in an aqueous solution, cause proteins present therein to unfold and nucleic acids to loose secondary structure. It is thought that chaotropic ions have these effects because they disrupt hydrogen-bonding networks that exists in liquid water and thereby make denatured proteins and nucleic acids thermodynamically more stable than their correctly folded or structured counterparts. Chaotropic ions include guanidinium, iodide, perchlorate and trichloroacetate. Chaotropic agents include guanidine hydrochloride, guanidine thiocyanate (which is sometimes referred to as guanidine isothiocyanate), sodium iodide, sodium perchlorate, and sodium trichloroacetate.

The term "substantially free of chaotropic agents" as used herein means that the concentration of chaotropic agents in the first equilibration buffer and in the first solution is sufficiently low that the first silica matrix preferentially forms a complex with the endotoxins, and leaves the target nucleic acid in solution. The concentration of chaotropic agent in the first equilibration buffer and in the first solution is preferably no higher than 200 mM, more preferably no higher than 100 mM, and most preferably no higher than 50 mM. The first equilibration buffer is preferably water, more preferably deionized or distilled water, even more preferably nanopure water.

Furthermore, the first solution and the first equilibration buffer preferably do not contain any binding reagent in any concentration which would be likely to promote formation of a complex between the target nucleic acid and the first silica matrix. Such binding promoters include chaotropic agents, high concentration of chaotropic or non-chaotropic salts, low molecular weight alcohols, or combinations of any of the above. Smaller concentrations of each promoter are required to promote complex formation, when any one promoter is combined with another. When a low molecular weight salt is present in the first solution or first equilibration buffer without any other binding agents, it can promote the formation of a complex between the nucleic acid and the first silica matrix, if the percent of alcohol by weight in the first solution or first equilibration buffer is at least 30%, when the low molecular weight alcohol is more polar than most other such alcohols, such as isopropanol, or at least 60% when the low molecular weight alcohol is less polar than most other such alcohols, such as ethanol.

The first solution provided in step (b) of the present method contains endotoxins and a target nucleic acid. The first solution can be any solution containing endotoxins and any target nucleic acid. The first solution is preferably obtained by disrupting a cell, such as a gram-negative bacteria cell such as an *E coli cell*, which contains or has endotoxins associated therewith. Any conventional method can be used to isolate the target nucleic acid from other material in the cell. But, the particular method used to isolate the target nucleic acid will depend upon whether the target is DNA or RNA. For example, a solution containing at least 1 M concentration of a chaotropic agent can be used to disrupt cells to isolate RNA. But, the same high concentration of the same chaotropic agent will denature and degrade most forms of DNA. By the same token, the same cells can be lysed with a strongly alkaline solution to release DNA contained therein, while RNA present in the same cell is degraded at the same high pH.

The first solution can be any one of the solutions of disrupted cells obtained as described above, provided the solution is processed to remove one or more of the binding promoter agents described above, if necessary. However, the first solution is more preferably obtained by processing a solution of lysed or disrupted cells to remove cellular debris and other material in the solution, such as lipids or proteins. Any one of a number of possible means can be used to extract such material from the solution of lysed or disrupted cells, including but not limited to precipitation of proteins, lipids, and chromosomal DNA by the addition of a low pH acetate buffer, phenol/chloroform extraction, and precipitation of the target nucleic acid with a low molecular weight alcohol, such as ethanol or isopropanol.

At least some of the endotoxins in the first solution, preferably all the detectable endotoxins contained therein, form a complex with the first silica matrix when the first solution is combined therewith. At least some, preferably all, the target nucleic acid in the first solution remains in the solution and does not form a complex with the first silica matrix. The endotoxin/first silica matrix can be separated from the resulting solution, the second solution, using any one of a number of possible removal means, depending upon the nature of the first silica matrix. The most preferred form of first silica matrix used in the matrix is a silica magnetic particle, and the most preferred means for separating such a particle from the solution after formation of the endotoxin/silica magnetic particle complex is using magnetic force. The second solution has a lower concentration of endotoxins than the first solution.

The concentration of endotoxins in the second solution can be further reduced by additional processing of the first or second solution. The additional processing can be a repetition of the endotoxin reduction steps outlined above, or use of known endotoxin reduction methods prior to or subsequent to endotoxin reduction according to the steps described above. Known endotoxin reduction methods suitable for use in conjunction with the present method include digestion extraction with Triton X-114, and contact with an endotoxin affinity adsorption resin (e.g. Sepharose or agarose bound to polymyxin B or histidine).

The target nucleotide can also be further purified using any one of a number of known methods for isolating the target nucleotide from materials, other than endonucleotides, in a solution. The method selected for use in isolating the target nucleotide will depend on the type of target nucleotide to be isolated and on the nature of the other materials in the solution from which the target nucleotide is to be isolated. For example, plasmid DNA can be isolated using isolation means such as: banding by ultracentrifugation in a cesium chloride/ethidium bromide solution; phenol, chloroform, or phenol/chloroform extraction; adherence to a silica matrix and elution therefrom after separation of the silica matrix from the solution in which the plasmid DNA was adhered to the matrix; removal of contaminants from the plasmid DNA solution by precipitation; removal of plasmid DNA from the solution by precipitation with a low molecular weight alcohol; preparatory gel electrophoresis; or liquid or high performance chromatography with a size exclusion gel. Chromosomal DNA can be isolated using most of the same means used to isolate plasmid DNA, except a cesium chloride gradient, but the conditions used in each isolation step are designed to favor isolation of the large chromosomal DNA molecules, rather than comparatively small plasmid molecules. RNA isolation requires the use of another set of extraction or other conditions, as RNA molecules are single-stranded and prone to digestion by RNase contaminants. When the target nucleic acid is a particular type of nucleic acid with a sequence which can be probed, an oligonucleotide probe can be used to isolate the target nucleic acid. For example, mRNA can be isolated from a solution of other nucleic acids using a substrate which can preferentially bind to mRNA in the solution when combined therewith, and be removed therefrom, such as magnetic silica particles with oligo dT attached thereto.

In a preferred embodiment of the present invention, the target nucleic acid is isolated from the second solution using a second silica matrix. The second silica matrix preferably comprises silica in the form of a resin, in the form of or embedded into a filter, or in the form of a silica particle, more preferably a silica gel particle, and even more preferably a silica magnetic particle. Suitable material for use as the second silica matrix is commercially available in forms which include, but are not limited to, Glass Milk controlled pore glass particles from Bio101, silica resins provided in QIAtip filters from QIAGEN, silica containing filters in QIAGEN spin columns, the Wizard® DNA isolation resins from Promega, MagneSil™ paramagnetic particles from Promega, and BioMag® magnetic silica particles from PerSeptive.

The second silica matrix is preferably equilibrated in a second equilibration buffer prior to use to isolate the nucleic acid according to this particular embodiment of the method of this invention. The second equilibration buffer is preferably configured to enhance binding of the nucleic acid to the second silica matrix, while inhibiting binding of endotoxins to the second silica matrix. The second equilibration buffer preferably comprises at least 200 mM, more preferably at least 1 M, and most preferably at least 2 M of a chaotropic agent. The chaotropic agent used in the second equilibration buffer is preferably a guanidinium salt, most preferably guanidine thoicyanate.

The target nucleic acid is preferably isolated from a solution from which endotoxins have been removed according to first part of the method of the present invention described above, i.e. the second solution, by combining the second solution with the second silica matrix in the presence of a binding agent, thereby forming a binding solution. The binding agent used in this step of this embodiment of this method is selected for its capacity to promote the formation of a complex between the target nucleic acid and the second silica matrix. In one embodiment of this aspect of the method, the binding agent is selected for its capacity to promote a link between the silica of the second silica matrix and the target nucleic acid. In such a case, the binding agent is preferably selected from the group consisting of: a chaotropic agent, a salt which is not a chaotropic agent, a low molecular weight alcohol, or a combination of the above. The proportions of each binding agent used depend upon how much of each other agent is present in the resulting binding solution. When only a non-chaotropic salt, such as sodium chloride, potassium chloride, or potassium acetate is used, the concentration of salt in the binding solution is preferably at least 500 mM. Smaller concentrations of non-chaotropic salt and other binding agents can be used where more than one binding agent is present in the binding solution.

When only a chaotropic agent is used, the final concentration of chaotropic agent in the binding solution is preferably at least 100 mM, more preferably at least 200 mM, and most preferably at least 500 mM. The concentration of chaotropic agent in the binding solution formed in the practice of the present method is preferably between about 0.1 M and 7 M, but more preferably between about 0.5 M and 5 M.

When a chaotropic agent is the only binding agent in a binding solution, the concentration of chaotropic agent therein must be sufficiently high to cause the nucleic acid to form a complex with the second silica matrix, but not so high as to substantially denature, degrade, or cause the target nucleic acid to precipitate out the binding solution. Large molecules of double-stranded DNA, such as chromosomal DNA, are stable ar chaotropic agent concentrations between 0.5 and 2 molar, but are known to precipitate out of solution at chaotropic agent concentrations about 2 molar. See, e.g. U.S. Pat. No. 5,346,994 issued to Piotr Chomczynski, column 2, lines 56–63. Contrastingly, RNA and smaller molecules of DNA such as plasmid DNA, restriction or PCR fragments of chromosomal DNA, or single-stranded DNA remain undegraded and in solution at chaotropic agent concentrations between 2 and 5 molar. Preferred chaotropic agents for use in promoting the formation of a complex between the target nucleic acid and the second silica matrix in a preferred embodiment of the method are guanidinium salts, more preferably guanidine hydrochloride.

When a low molecular weight alcohol is the only binding agent present in the binding solution, the minimum amount of alcohol necessary to promote formation of the complex between the second silica matrix and the nucleic acid depends upon the nature of the alcohol and on the type of nucleic acid to form the complex with the second silica matrix. Lower concentrations of polar alcohols, such as isopropanol, can cause RNA to preferentially complex with isolated from the second solution. Specifically, RNA tends to form a complex with the second silica matrix more readily than DNA, in the presence of binding solution concentrations of polar low molecular weight alcohols such as isopropanol, of up to 30% by volume. DNA preferentially forms a complex with the second silica matrix at polar low molecular weight alcohols of over 30% by volume. Both RNA and DNA complex with the second silica matrix at les polar low molecular weight alcohol, such as ethanol, concentrations of at least 50%, but do so more readily when the. When the only binding agent in the binding solution is something other than a chaotropic agent, it is preferably a low molecular weight alcohol, more preferably a less polar alcohol such as ethanol at a concentration of at least 80%. The low molecular weight alcohol used as a binding agent is preferably ethanol or isopropanol.

Once the second silica matrix and target nucleic acid have been combined in the presence of the binding agent, and a nucleic acid/matrix complex has been permitted to form therein, the second silica matrix and complex are separated from the nucleic acid solution. The means used to separate the second silica matrix from the second solution depends upon the nature of the second silica matrix. For example, if the second silica matrix is a silica magnetic particle, it can be separated from the solution using magnetic force, filtration, or centrifugation. If the second silica matrix is a filter, gravity or vacuum filtration can be used, depending upon the configuration of the filter and any support structure associated therewith. If the second silica matrix is a resin or silica gel particles, it can be removed by any one of the means cited above except, perhaps, by magnetic force.

As an optional additional step in isolating the target nucleic acid once it forms a complex with the second silica matrix, the second silica matrix and complex can be washed in a wash solution after removal from the second solution. A wash solution is preferably selected for use in the wash step which can remove contaminants from the matrix and complex without eluting the target nucleic acid therefrom. The wash solution used preferably contains at least 30% and up to 60% by weight of a polar low molecular weight alcohol such as isopropanol when the target nucleic acid is RNA, at least 60% by weight of the polar low molecular weight alcohol when the target nucleic acid is DNA; and at least 60% by weight, more preferably at least 80% by weight of a less polar low molecular weight alcohol such as ethanol when the target nucleic acid is either RNA or DNA.

Once the second silica matrix and nucleic acid/matrix complex have been separated from the second solution, and washed if a washing step is included, the target nucleic acid is eluted from the complex. Elution is accomplished by exposing the complex to an elution solution configured to release the target nucleic acid from the target. When the association between the silica and target nucleic acid components of the matrix is a direct association, the elution solution is preferably an aqueous solution of low ionic strength which is substantially free of chaotropic agents, such as water or an aqueous solution with a non-chaotropic salt concentration of less than 200 mM. In such cases, the elution solution is more preferably demonized or distilled water or TE buffer or, most preferably, nanopure water.

When the association between the silica and target nucleic acid components of the nucleic acid/matrix complex is through a probe, such as an oligonucleotide probe, which is associated with the nucleic acid through hydrogen bonds, the elution solution must contain components or be used under conditions which promote disassociation of the hydrogen bonds. For example, solution temperatures above 70° C. can cause an oligonucleotide to disassociate from a complementary sequence. If heat is not used, an elution solution with a strong base can cause hydrogen bonds between an oligonucleotide and a target DNA molecule to disassociate. RNA can be disassociated from an oligonucleotide in an elution solution containing a chaotropic agent concentration of at least 100 mM, more preferably at least 200 mM.

Once the target nucleic acid has been eluted from the nucleic acid/matrix complex, it can be isolated further using conventional methods of isolation, if additional purification is desired. However, the nucleic acid material isolated according to the preferred method of the present invention described above is suitable, without further isolation, for analysis or further processing by molecular biological procedures. The eluted nucleic acid can be analyzed by, for example, sequencing, transfection, restriction enzyme analysis, or nucleic acid probe binding. Thus, the methods of the invention can be applied as part of methods, based on analysis of DNA or RNA, for, among other things, diagnosing diseases; identifying pathogens; testing foods, cosmetics, blood or blood products, or other products for contamination by pathogens; forensic testing; paternity testing; and sex identification of fetuses or embryos.

The following, non-limiting examples teach various embodiments of the invention. In the examples, and elsewhere in the specification and claims, volumes and concentrations are at room temperature unless specified otherwise. Various silica matrices, including silica gel particles, SOCM magnetic silica particles, and diatomaceous earth, were used to remove endotoxins from and to isolate plasmid DNA from lysates of various strains of $E$ $coli$ bacteria transformed with the plasmid DNA. One skilled in the art of the present invention will be able to use the teachings of the present disclosure to select and use silica matrices other than the particular matricies used to remove endotoxins and to isolate nucleic acids in the particular illustrations of the methods of the present invention demonstrated in the Examples, below. The Examples should not be construed as limiting the scope of the present invention.

The SOCM particles used in the Examples below, also referred to below as "magnetic silica particles" or as "MagneSil™" particles, were taken from either of two batches of particles. The SOCM particles in the first batch were found to have the following physical characteristics: surface area of 55 $m^2/g$, pore volume of 0.181 ml/g for particles of <600 Å diameter, pore volume of 0.163 ml/g for particles of >600 Å diameter, median particle size of 5.3 $\mu$m, and iron leach of 2.8 ppm when assayed as described herein above using ICP. The particles in the other batch of SOCM were found to have the following characteristics: surface area of 49 $m^2/g$, pore volume of 0.160 ml/g (<600 Å diameter), pore volume of 0.163 ml/g (>600 Å diameter), median particle size of 5.5 $\mu$m, and iron leach of 2.0 ppm.

EXAMPLE 1

Preparation of Lysate $E$ $coli$ bacteria cells, either JM109 or DH5α strains of $E$ $coli$, as indicated below, were transformed with pGL3-Control Vector (Promega) plasmid DNA and grown in an overnight culture of Luria Broth ("LB") medium at 37° C., then harvested by centrifugation. The following solutions were used to prepare a lysate of the harvested cells, as described below:

Cell Resuspension Solution
    50 mM Tris-HCl, pH 7.5
    10 mM EDTA
    100 $\mu$g/ml DNase-free ribonuclease A (RNase A)
Neutralization Buffer
    1.32M KOAc (potassium acetate), pH 4.8 thiocyanate
Cell Lysis Solution
    0.2 M NaOH
    1% SDS (sodium dodecyl sulfate)

A cleared lysate of the transformed cells was produced as follows:

1. The cells from 1 to 10 ml of bacteria culture were harvested by centrifuging the culture for 1–2 minutes at top speed in a microcentrifuge. The harvested cells were resuspended in 250 $\mu$l of Cell Resuspension Solution, and transferred to a microcentrifuge tube. The resulting solution of resuspended cells was cloudy.

2. 250 $\mu$l of Cell Lysis Solution was then added to the solution of resuspended cells and mixed by inversion until the solution became relatively clear, indicating the resuspended cells had lysed.

3. 350 $\mu$l of Neutralization Buffer was added to the lysate solution, and mixed by inversion. The lysate became cloudy after the Neutralization Solution was added.

4. The solution was then spun in a microcentrifuge at top speed for 5 minutes to clear the lysate.

5. The resulting supernatant of cleared lysate was transferred to a new microcentrifuge tube.

Samples of the cleared lysate solution from step 5 and the uncleared lysate after addition of the neutralization solution according to step 3, above were then exposed to various silica matrices under different conditions, according to Examples 4–6 below. Each sample was tested for endotoxins according to Example 2, and for plasmid DNA yield and quality according to the procedures described in Example 3.

EXAMPLE 2

Endotoxin Assays

A limulus amoebocyte lysate (LAL) gel precipitation assay, was conducted to determine the number of units of endotoxin in bacteria lysate samples taken before and after the lysate solutions came into contact with one or more of the silica matricies tested in Examples below. E-TOXATE®, from SIGMA® (St. Louis, Mich., cat. no. 210-D1) was used as the amoebocyte lysate standard for this series of LAL assays. E-TOXATE® is described in the 1997 SIGMA® Catalog ( p. 448) as "(Amoebocyte lysate; Horseshoe crab lysate) from *Limulus polyphemus*". Endotoxin-free water ("ETF water") was used in all the steps of this assay, including all the dilution steps. Each sample or set of samples was assayed according to the following procedure:

1. Samples were prepared for serial dilution, with a larger initial dilution factor used (e.g., 1:10000 or higher) for samples which had not been in contact with any endotoxin removal agent, such as silica gel particles, and with smaller initial dilutions of 1:500 to 1:1000 for samples which had come into contact with such agents. Endotoxin-free ("ETF") water was used for all dilutions described herein.
2. 2 X Serial dilutions were prepared of each sample as follows. 25 µl of each sample added to 25 µl of ETF water in the first set of wells of 96 well microtiter plate, and mixed by pipetting. 25 µl of that diluted solution was then transferred to a second well with another 25 µl of ETF water, and so on until a series of 12 samples has been prepared per sample.
3. A series of dilutions of endotoxin standard were prepared as follows. First, the contents of a fresh bottle of Endotoxin Standard (SIGMA® cat. no. 210-SE) were diluted with ETF water, in accordance to the manufacturer's instructions on the bottle. Second, the following volumes of ETF water were added to each of a series of nine (9) 1.5 ml microcentrifuge tubes as follows: 900 µl to tubes 1–3, 1,050 µl to tube 4, and 500 µl to tubes 5–9. Third, 100 µl of the Endotoxin Standard from the bottle diluted as described above was transferred to tube 1, mixed, and then serially diluted as follows:
   100 µl from tube 1 was added to tube 2 and mixed, for 40 Endotoxin Units ("EU") per milliliter (ml.),
   100 µl from tube 2 was added to tube 3 and mixed, for 4 EU/ml,
   150 µl from tube 3 was added to tube 4 and mixed, for 0.5 EU/ml,
   500 µl from tube 4 was added to tube 5 and mixed, for 0.25 EU/ml,
   500 µl from tube 5 was added to tube 6 and mixed, for 0.125 EU/ml,
   500 µl from tube 6 was added to tube 7 and mixed, for 0.06 EU/ml,
   500 µl from tube 7 was added to tube 8 and mixed, for 0.03 EU/ml,
   500 µl from tube 8 was added to tube 9 and mixed, for 0.015 EU/ml.
4. The Endotoxin Standards diluted as described above and a blank standard were then transferred to a microtiter plate as follows: 25 µl ETF water (blank) in column 1, 25 µl from standard tube 4 in column 2, 25 µl from standard tube 5 in column 3, 25 µl from standard tube 6 in column 4, 25 µl from standard tube 7 in column 5, 25 µl from standard tube 8 in column 6, and 25 µl from standard tube 9 in column 7.
5. A fresh bottle of E-TOXATE®, i.e. LAL in lyophilized form, was opened for every two microtiter plates of samples or standards to be tested. ETF water was added to each bottle of E-TOXATE® to a final concentration contains, and an amount of ETF water was added to each bottle to bring about 5 ml of ETF water was added to each bottle. When multiple bottles of E-TOXATE® were opened for a single set of assays, the bottle contents were resuspended in ETF water, as described immediately above, and combined prior to use. 25 µl of E-TOXATE® was added to each well of each microtiter plate containing a sample, standard, or blank.
6. Once E-TOXATE® had been added to each well, the microtiter plate was covered, and the plate placed in a 37° C. oven for 1 hour (+/−5 minutes), during which time the E-TOXATE solution will gel in the presence of a sufficiently high amount of endotoxin.
7. The microtiter plate was then removed from the oven, examined for gelation, and the last well in each column with gelation (i.e. positive result) was noted. The following formula was used to determine the EU/ml of the original sample tested in each column:

EU/ml=1 /(highest dilution of sample which tests positive) ×(highest dilution of standard which tests positive)

For example, if the sample was positive (i.e. gel found) at a dilution of 1/4000, but was negative (i.e. no gel found) at a dilution of 1/8000, and the standard was positive at 0.06 dilution and negative at 0.03, then the EU/ml is determined as follows: EU/ml=1/(1/4000)×0.06=240 EU/ml.

EXAMPLE 3

Assay of Plasamid DNA Quality and Quantity

Plasmid DNA isolated by binding and release from magnetic silica particles according to Example 3 was assayed further to determine the quantity and quality of the DNA isolated thereby. Specifically, the plasmid DNA was assayed qualitatively using gel electrophoresis, and quantitatively using a spectrophotometer.

The gel assay results showed a high percentage of intact, supercoiled plasmid DNA present in the sample.

The optical density measurements accurately reflected DNA yield, as evidenced by absorbance ratios (ex. 260/250 nm and 260/280 nm) in the expected range for DNA.

EXAMPLE 4

Lysate Exposed to ETF Water vs. Guanidine Thiocyanate Equilibrated Magnetic Silica Particles Two different samples of SOCM particles were prepared from the same batch of particles as follows. One sample of SOCM particles was suspended in ETF water for a final concentration of 100 mg of particles per milliliter of water. The other sample of SOCM particles was suspended in a Guanidine Thiocyanate solution, for a final concentration of 100 mg particles per ml of 5 M Guanidine Thiocyanate buffer. Aliquots of each of the samples of equilibrated SOCM particles was used to remove endotoxins from and to isolate plasmid DNA from a cleared lysate prepared according to Example 1, above.

1. 100 μl of the particles suspended in ETF water or in 3 M GTC, as indicated below, were added to each 900 μl of cleared lysate in a first tube.
2. The first tube was then placed in a separation rack with a magnet on one side (a MagneSphere® magnetic separation stand(Promega)), where the magnetic particles migrated to the surface of the tube closest to the magnet. The solution was decanted out of the tube and either discarded, or processed again by repeating steps 1 and 2 adding a new aliquot of the magnetic silica particles to the lysate in step 1 in preparation for the second binding step 2, above. The remaining steps, below were carried out on the first particles after a first initial binding step described herein, or on the particles added in the optional second binding reaction.
3. The first tube was then removed from the rack, and the particles remaining therein were resuspended in 1×W440 Wash Solution (4 M guanidine hydrochloride in 40% Isopropanol). The first tube was then returned to the separation rack, and the wash solution discarded therefrom. The wash step was repeated using a second wash solution of 80% ethanol.
4. Finally, the particles remaining in the first tube after the last wash step were resuspended in water. The first tube was returned to the separation rack, and the water carefully decanted therefrom into a second tube.

The same five steps described above were also performed using an endotoxin standard solution in Neutralization Solution, as a control.

Samples were taken of: (1) the cleared lysate or endotoxin standard solution prior to addition of any particles thereto, (2) the cleared lysate or standard solution after the particles had been added to the lysate and removed therefrom by magnetic force, and (3) the ETF water after elution from the particles in the final step, above (i.e. step 5). Each of the samples was then tested for endotoxin concentration, according to the assay procedure described in Example 2, above. Table 1, below, provides a summary of the results.

TABLE 1

| Experiment | Lysate or Std. Solution (EU/ml) | Solution After Particles (EU/ml) | Eluant (EU/ml) |
| --- | --- | --- | --- |
| Lysate Assay Results: | | | |
| particles in GTC, | $256 \times 10^3$ | $256 \times 10^3$ | $16 \times 10^3$ |
| first binding | $512 \times 10^3$ | $256 \times 10^3$ | $2 \times 10^3$ |
| particles in GTC, | $256 \times 10^3$ | $36 \times 10^3$ | $16 \times 10^3$ |
| second binding | $256 \times 10^3$ | $64 \times 10^3$ | $1 \times 10^3$ |
| particles in H$_2$O, | $256 \times 10^3$ | $36 \times 10^3$ | $16 \times 10^3$ |
| first binding | $512 \times 10^3$ | $64 \times 10^3$ | |
| particles in H$_2$O, | $8 \times 10^3$ | $1,024 \times 10^{3}*$ | $8 \times 10^3$ |
| second binding | $64 \times 10^3$ | $16 \times 10^3$ | $8 \times 10^3$ |
| Endotoxin Standard Assay Results: | | | |
| particles in GTC, | $0.80 \times 10^3$ | $3.2 \times 10^3$ | 2.5 |
| single binding | $2.0 \times 10^3$ | $0.51 \times 10^3$ | 0.2 |
| particles in H$_2$O, | $0.80 \times 10^3$ | $6.4 \times 10^3$ | $1.3 \times 10^3$ |
| single binding | $2.0 \times 10^3$ | $1.0 \times 10^3$ | 0.05 |

The assay results displayed in Table 1, above, clearly demonstrate that magnetic silica particles equilibrated in ETF water tend to bind significantly higher amounts of endotoxin in a single binding step than do magnetic silica particles equilibrated in a GTC solution. The results also show that twice as much endotoxin can be removed from a solution using two particle binding steps, even when particles equilibrated in ETF water are employed. The results indicated with an asterisk above appear to be anomalous.

EXAMPLE 5

Guanidine Thiocyanate in Neutralization Buffer vs in Magnetic Silica Particles

A second experiment, similar to Example 4 above, was done to determine whether GTC would have a similarly, inhibitory effect on endotoxin binding to magnetic silica particles if GTC were present in the lysate but not in the magnetic silica particles prior to combination therewith. Particles equilibrated in a solution of 3 M GTC, as described in Example 4, were combined with a cleared lysate in Neutralization Solution without GTC prepared as described in Example 1, above, as a control. Another set of particles was equilibrated in ETF water, as described in Example 4, and combined with a cleared lysate solution prepared as described in Example 1, except that the Neutralization Solution used therein contained 3 M guanidine thiocyanate. Both sets of particles and neutralization solutions were processed as described in Example 4, with only a single particle binding step.

Samples were taken of the lysate solution before and after binding to each set of particles, and a third set of samples was taken of the eluent obtained from the particles after addition of ETF water thereto. Two sets of samples were assayed. Table 2, below shows the results of this experiment.

TABLE 2

| Experiment | Lysate or Std. Solution (EU/ml) | Solution After Particles (EU/ml) | Eluant (EU/ml) |
| --- | --- | --- | --- |
| particles in GTC, no GTC in Neut. Solution | $1,024 \times 10^3$ | $1,024 \times 10^3$ $1,024 \times 10^3$ | $32 \times 10^3$ $1.28 \times 10^3$ |
| particles in H$_2$O, GTC in Neut. Solution | $1,024 \times 10^3$ | $128 \times 10^3$ $128 \times 10^3$ | $2 \times 10^3$ $32 \times 10^3$ |

The results in Table 2 indicate that guanidine thiocyanate adversely affects the capacity of magnetic silica particles to remove endotoxins from a cleared lysate solution when the guanidine thiocyanate is present in the particles prior to addition to the lysate, but not when it is present in the lysate but not in the particles.

EXAMPLE 6

Silica Gel Particle and Silica Magnetic Particle Addition to Cleared vs Non-Cleared Lysate Separate suspensions were prepared of silica gel particles and magnetic silica particles (SOCM particles) in ETF water, for a final concentration of 10 mg/ml for each suspension. Both the magnetic and non-magnetic particles have similar particle size, pore size and composition. Four different sets of samples were prepared, with three samples per set, as follows:

Set 1: 150 μl of silica gel particle suspension was added to 750 μl of lysed, neutralized cells prepared as described in Example 1, incubated for 5 minutes at room temperature, then spun in a microfuge for 10 minutes. The resulting cleared lysate supernatant was removed and tested for endotoxin content, as described in Example 1, above.

Set 2: 150 μl of magnetic silica particle suspension was added to 750 μl of lysed, neutralized cells prepared as described in Example 1, and processed in the same way as the samples in Set 1.

Set 3: 150 μl of silica gel particle suspension was added to 750 μl of cleared lysate prepared as described in Example 1, and processed the same way as the samples in Set 1.

Set 4: 150 μl of magnetic silica particle suspension was added to 750 μl of cleared lysate prepared as described in Example 1, and processed in the same way as the samples in Set 1.

Table 3, below summarizes the endotoxin analysis results obtained from the sample sets described herein above. Each number in the table is an average of the results obtained from all three samples in each set.

TABLE 3

| Sample/Control Test | Lysate Before Particles (EU/ml × $10^3$) | Lysate After Particles (EU/ml × $10^3$) |
| --- | --- | --- |
| Silica Gel Particles in Uncleared Lysate | 368 | 166 |
| Magnetic Silica Particles in Uncleared Lysate | 204 | 256 |
| Silica Gel Particles in Cleared Lysate | 512 | 64 |
| Magnetic Silica Particles in Cleared Lysate | 614 | 64 |

From the results in Table 3, it appears the magnetic silica particles were ineffective at removing endotoxins from the uncleared lysate solution when added directly thereto, while the silica gel particles were only slightly effective at doing so. Contrastingly, both types of particles effected about a ten-fold decrease in the concentration of endotoxins in a cleared lysate, when added thereto.

EXAMPLE 7

Scale up of Magnetic Silica Particles Used in Endotoxin Removal from Two Different Bacteria Cell Cultures Increasing quantities of magnetic silica particles equilibrated in ETF water were added to lysates from the same volume of overnight cultures of bacteria cells, after addition of a Neutralization Solution, and after clearance of the lysate by centrifugation or magnetic separation as described in Examples 6 or 3 above, to determine the minimum range of particle quantity needed to optimize endotoxin removal for each volume and strain of culture. For example, 0 mg, 4 mg, 8 mg, 16 mg, and 20 mg of particles suspended in ETF water, were added to 10 ml of cleared lysates from two different strains of E coli bacteria cells (JM109 and DH5α) transferred with pGL-3 control vector in Neutralization Solution with 3 M Guanidine Thiocyanate. Each cleared lysate solution was incubated for 5 minutes at room temperature after the particles were added thereto, spun in a centrifuge followed by separation of the particles by magnetic force, and decanted to separate the solution from the particles. The resulting treated lysate solution was then assayed to determine the amount of endotoxin contained therein, according to the procedure described in Example 2.

The results of each optimization experiment, such as the one described above, were plotted to determine the optimal amount of particles to add to a given volume of any given strain of bacteria. FIG. 1 is a plot of the results of the particular experiment described above, performed with a 10 ml culture of each of two different strains of bacteria cells. FIG. 1 clearly shows that endotoxin can be removed from that volume of culture using 4 to 6 mg of magnetic silica particles.

EXAMPLE 8

Assay of Efficiency of Endotoxin Removal with Magnetic Silica Particles, with Increased Culture Volume Amounts of magnetic silica particles (equilibrated in ETF water) determined as described in Example 7 for each of three different volumes of E coli bacteria culture(DH5α calls transformed with pGL3 control vector), specifically for 1 ml, 10 ml, and 250 ml of culture, were added to cleared lysates of each culture prepared as described in Example 1 above, wherein the procedure of Example 1 was proportionally scaled up to accommodate the larger volumes of culture processed therein. Each lysate sample was treated with the amounts of magnetic silica particles in ETF water determined as described above followed by binging to magnetic silica particles equilibrated in 3 M GTC, washing, and elution as described in Example 4, above, after adjusting volumes to scale.

The results of this experiment are provided in Table 4, below.

TABLE 4

| Prep. Size | EU in Lysate | EU in Supernatant | % Purification |
| --- | --- | --- | --- |
| 1 ml | 10.9 × $10^3$ | 760 | 93 |
| 1 ml | 21.8 × $10^3$ | 760 | 96 |
| 10 ml | 1,741 × $10^3$ | 30.4 × $10^3$ | 98 |
| 10 ml | 435 × $10^3$ | 30.4 × $10^3$ | 93 |
| 250 ml | 17.4 × $10^6$ | 122 × $10^3$ | 99 |
| 250 ml | 17.4 × $10^6$ | 122 × $10^3$ | 99 |

From the results in Table 4, it appears the endotoxin removal procedure developed on the microliter scale with magnetic silica particles, as described in several of the Examples above, can be scaled up to remove endotoxins from lysates of considerably larger volumes of bacteria cell cultures.

EXAMPLE 9

Endotoxin Removal Capacity Assays with Silica Gel Particles and Diatomaceous Earth Two other silica-based materials were also tested for their capacity to remove endotoxins from a bacteria lysate solution under similar conditions to those used to remove endotoxins from the same type of solutions using magnetic silica particles in Examples, above. The two different silica-based materials used in this assay were: (1)silica gel particles of the same size and type used in Example 6, and (2) diatomaceous earth, acid washed and calcined.

The silica gel particles and diatomaceous earth particles were each suspended in ETF water for a final concentration of 100 mg of particles per milliliter of water. The particle suspensions were each diluted 1:2 serially. Cleared lysates of E Coli bacteria, bacteria which had not been transformed with plasmid DNA, were prepared as described in Example 1. A sufficient amount of cleared lysate was prepared for six sets of three test samples (particles added) and one set of two controls (no particles added). 75 µl of each diluted sample of suspended cells was added to 200 µl of cleared lysate for each test sample, and 75 µl of ETF water was added to each 200 µl of cleared lysate for each control sample. Each sample was then incubated for 5 minutes at room temperature, and then spun for 10 minutes in a microcentrifuge. The resulting supernatant was decanted and tested for endotoxin content, as described in Example 2.

Figure 2:
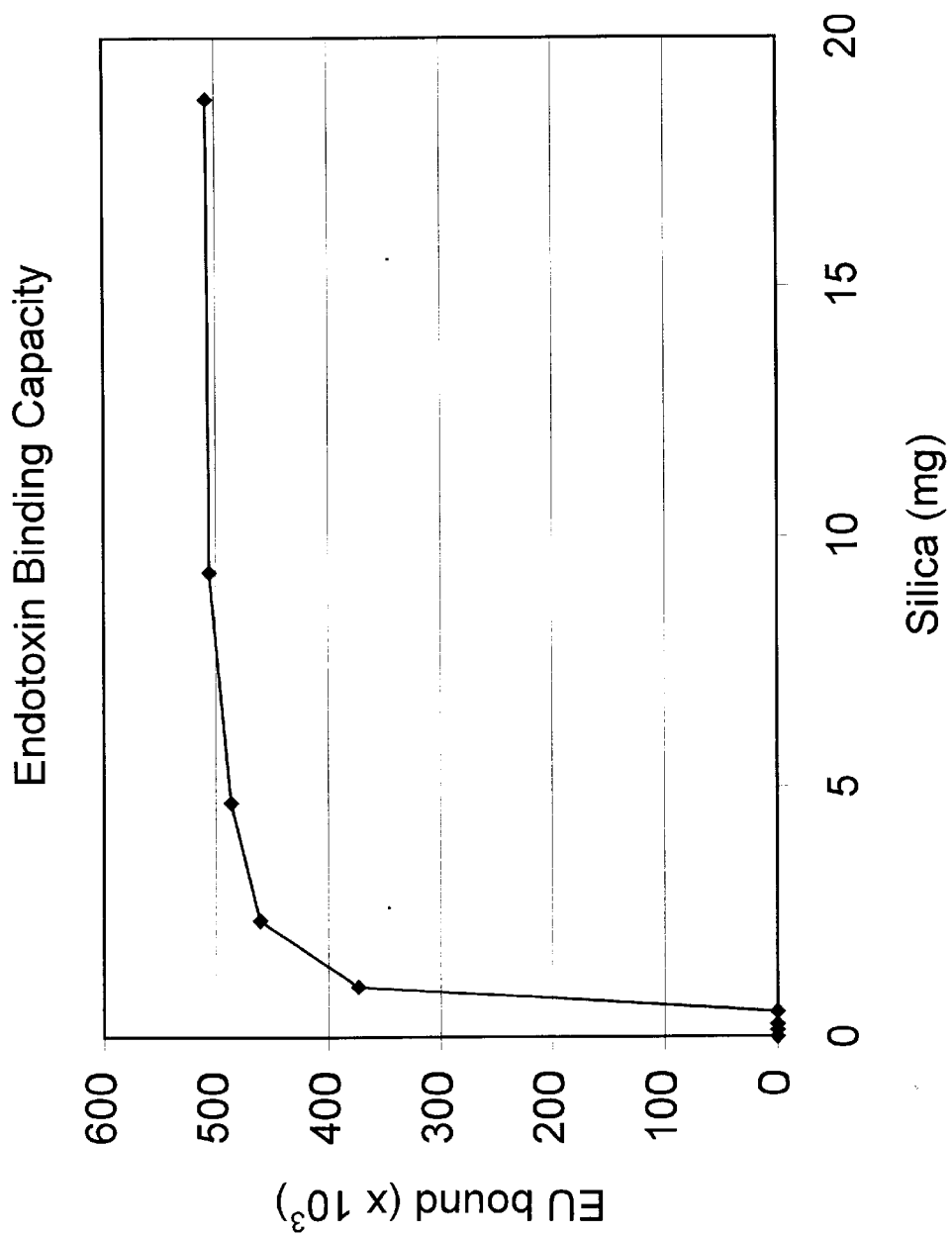
FIG. 2 is a plot of units of endotoxin bound vs the number of milligrams of diatomaceous earth added to a lysate of E coli DH5α bacteria cells transformed with plasmid DNA.
Figure 3:
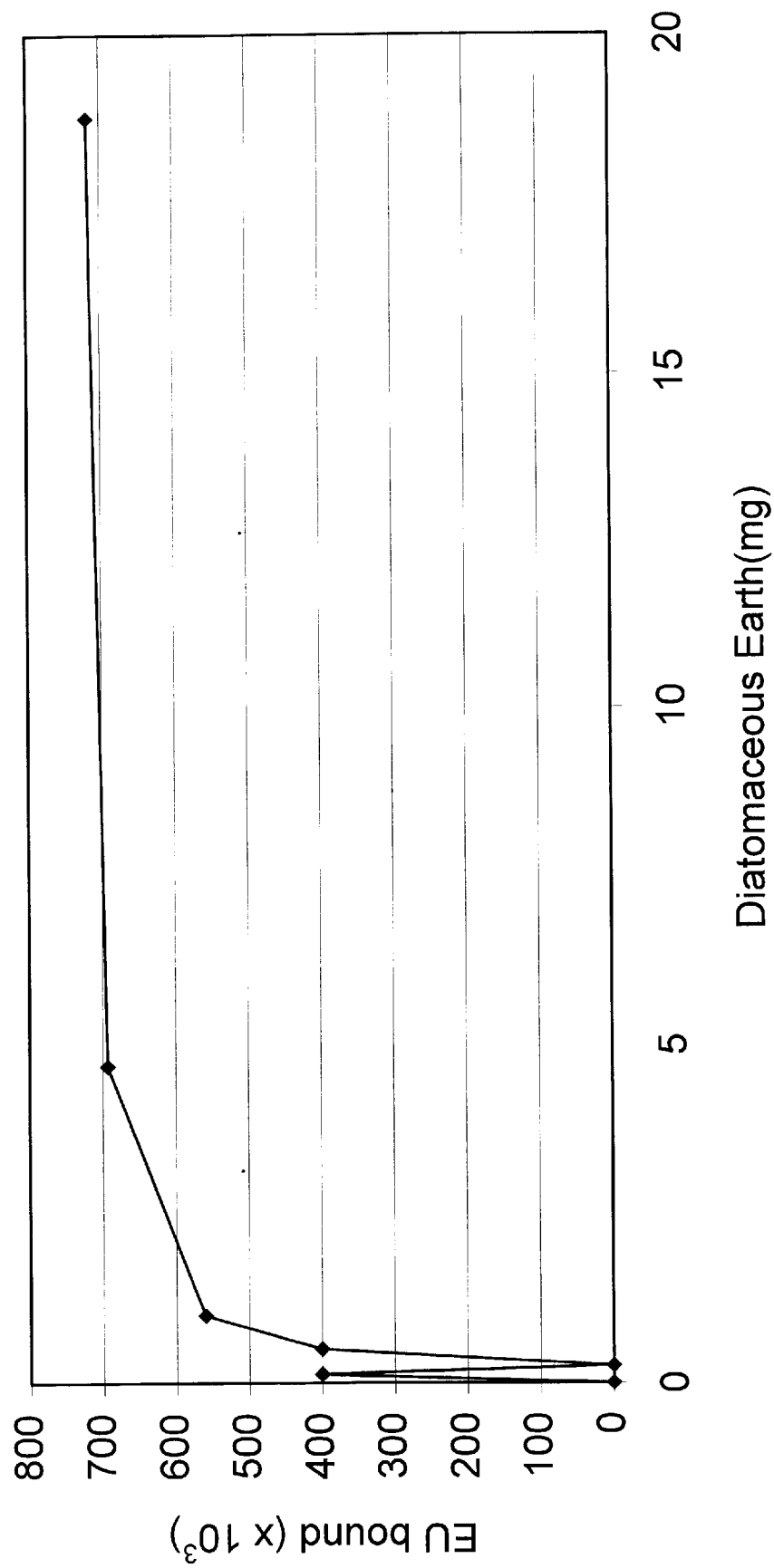
FIG. 3 is a plot of units of endotoxin bound vs the number of milligrams of non-magnetic silica based resin added to a lysate of E coli DH5α bacteria cells transformed with plasmid DNA.

The Endotoxin removal assay results obtained using silica gel particles were plotted in FIG. 2 in terms of the endotoxin units removed ("EU bound") vs the milligrams of silica gel particles added to each 200 µl of cleared lysate. Assay results obtained using diatomaceous earth are plotted in FIG. 3 in terms of endotoxin unites removed vs. milligrams of diatomaceous earth particles added per 200 µl of cleared lysate. The results plotted in FIGS. 2 and 3 are similar to one another. Both show a marked increase in the amount of endotoxin units removed from each lysate solution upon addition of each type of silica based particle, and the maximum number of endotoxin units removed with each type of particle is reached at about 5 mg of particle added.

EXAMPLE 10

Comparison of Standard Silica-Based Plasmid DNA Isolation Procedure and Present Endotoxin Removal Procedure The same volume (25 ml) of the same culture of *E coli* transformed with the same plasmid DNA was processed using two different plasmid isolation procedures. Four samples of the transformed bacteria culture were processed using each procedure. In the first such procedure, components of a QIAfilter Plasmid Maxi Kit from QIAGEN were used to isolate the plasmid DNA according to the manufacturer's instructions, specifically, according to the procedure provided in red on pages 22 to 25 of the QIAGEN Plasmid Purification Handbook (January 1997).

In the other procedure tested herein, magnetic silica particles were used to remove endotoxins from a cleared lysate obtained from an 25 ml culture, and to isolate the plasmid DNA therefrom according to the following general procedure, after scale up of all quantities used to reflect the larger volume of overnight culture processed:

1. 25 ml of overnight cultures of the bacteria were harvested by centrifugation, and resuspended in 2.5 ml of Resuspension Buffer.
2. 2.5 ml of Lysis Buffer was added to the resuspended cells and mixed by inversion, then incubated at room temperature for 5 minutes.
3. 3.5 ml of Neutralization Solution was added to each tube of lysed cells, mixed by inversion, and incubated 5 minutes at room temperature.
4. The lysate from step 3 was then centrifuged for 10 minutes, and the resulting cleared lysate supernatant was transferred to a fresh tube.
5. 1 ml of 100 mg/ml magnetic silica particles suspended in ETF water was added to the cleared lysate, and incubated at room temperature for 10 minutes.
6. The magnetic silica particles were separated from the cleared, treated lysate, using magnetic force, and the treated lysate was transferred to a fresh tube.
7. 3 ml of 50 mg/ml magnetic silica particles suspended in 3 M guanidine thicocyanate was added to the treated lysate, and incubated for 2 to 3 minutes.
8. The lysate was removed from the second set of magnetic silica particles added in step 7, using magnetic force, and the lysate was discarded.
9. The magnetic silica particles were washed four times in a wash solution of 80% ethanol, wherein the particles were separated from each wash solution after each wash step with magnetic force, and then heated for 4 minutes at 65° C. after the last wash step.
10. 1.5 ml of ETF water was added to the magnetic silica particles to elute plasmid DNA bound thereto after step 9, and the resultant eluant was separated from the particles by magnetic force.

Each sample eluted from the QIAfilter Cartridge according to the QIAGEN protocol used to process the first set of 25 ml cultures of transformed bacteria, and each sample eluted from the magnetic silica particles in the final step of the procedure described above was assayed for endotoxin units according to Example 2 and for plasmid DNA quantity and quality according to Example 3. Both elution procedures produced plasmid DNA which appeared to be substantially intact, when fractionated on a 1% agarose gel. The plasmid DNA solutions produced using both procedures was also similar in terms of being relatively free of protein contaminants, as all samples tested produced absorbance ratios of 260/280 nm of at least 1.80 (should be at least 1.7). The average yield of plasmid DNA from the QIAGEN protocol, as determined using the absorbance of the elution solution at 260 nm, was 203 µg, while the average yield of plasmid DNA from the protocol outlined above was 124 µg. The endotoxin units, adjusted to units per microgram of plasmid DNA isolated have been plotted out, and are depicted in FIG. 4 for all four samples isolated using each of the two procedures described above.

Figure 4:
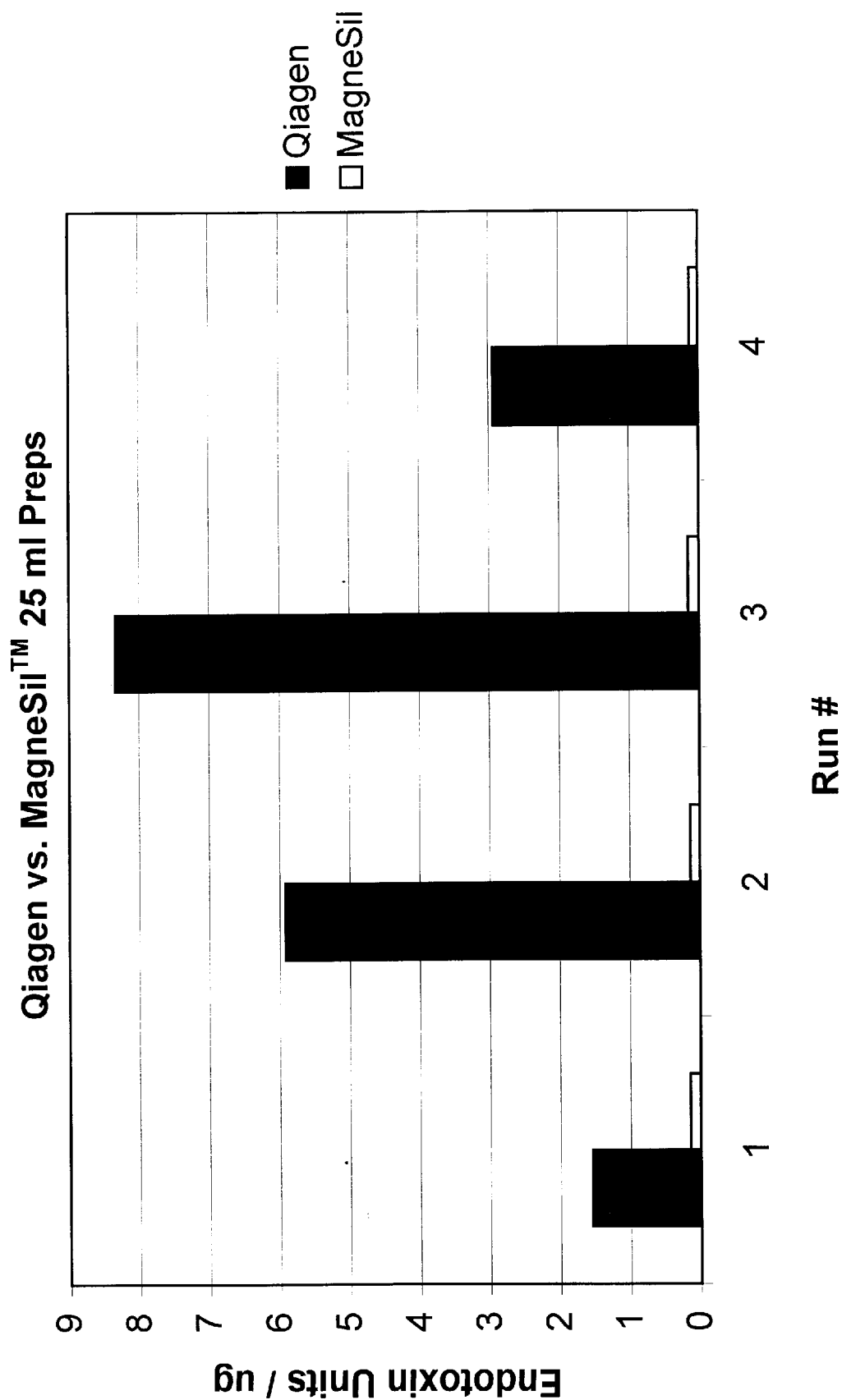
FIG. 4 is a plot of endotoxin units per pg of four samples each of plasmid DNA isolated using a QIAfilter Plasmid Maxi Kit (from QIAGEN, Inc.) using MagneSil™ magnetic silica particles (from Promega Corp.) according to a method of this invention.

FIG. 4 clearly indicates that the procedure described above removed a significant amount of endotoxin from each sample of 25 ml. culture compared to the QIAGEN plasmid DNA isolation method tested herein.

What is claimed is:

1. A method of reducing the concentration of endotoxins in a solution containing a target nucleic acid and endotoxins, the method comprising:

a. providing a first silica matrix consisting essentially of silica, wherein the first silica matrix is equilibrated with a first equilibration buffer, wherein the equilibration is substantially free of chaotropic agents;
   b. providing a first solution comprising a target nucleic acid and endotoxins, wherein the first solution is substantially free of chaotropic agents;
   c. combining the first silica matrix and the first solution, wherein at least one of the endotoxins forms an endotoxin/matrix complex with the first silica matrix, thereby producing a second solution which contains fewer of the endotoxins than are present in the first solution; and
   d. separating the second solution from the endotoxin/matrix complex.

2. The method of claim 1, wherein the first silica matrix provided in step (a) consists essentially of a filter impregnated with silica.

3. The method of claim 1, wherein the first silica matrix provided in step (a) is a resin consisting essentially of a silica material selected from the group consisting of diatomaceous earth, ground glass particles, and silica gel.

4. The method of claim 1, wherein an external force selected from the group consisting of centrifugation, filtration at atmospheric pressure, and vacuum filtration is used in step (d) to separate the endoxin/matrix complex from the second solution.

5. The method of claim 1, wherein the first silica matrix consists essentially of a silica gel particle.

6. The method of claim 1, wherein the first silica matrix consists essentially of a first silica magnetic particle.

7. The method of claim 6, wherein the endotoxin/matrix complex is separated from the second solution using a magnetic force.

8. The method of claim 1, wherein at least 90% of the target nucleic acid in the first solution is present in the second solution.

9. The method of claim 1, comprising the additional steps of:

providing a second silica matrix equilibrated with a second equilibration buffer;

combining the second solution with the second silica matrix in the presence of a target nucleic acid binding agent to form a binding solution, wherein the target nucleic acid forms a nucleic acid/matrix complex with the second silica matrix;

separating the second silica matrix and nucleic acid/matrix complex from the second solution; and eluting the nucleic acid from the nucleic acid/matrix complex.

10. The method of claim 9, wherein the second equilibration buffer comprises at least 100 mM concentration of a chaotropic agent.

11. The method of claim 9, wherein the binding agent is selected from the group consisting of a salt which is not a chaotropic agent, a low molecular weight alcohol, and a combination of the above.

12. The method of claim 9, wherein the binding agent comprises a chaotropic agent.

13. The method of claim 12, wherein the target nucleic acid is RNA and the concentration of the chaotropic agent in the binding solution is no more than 0.5 M.

14. The method of claim 12, wherein the target nucleic acid is DNA and the concentration of the chaotropic agent in the binding solution is at least 100 mM.

15. The method of claim 9, wherein the second silica matrix comprises a silica material selected from the group consisting of diatomaceous earth, ground glass, controlled pore glass, and silica gel.

16. The method of claim 9, wherein an external force is used to separate the second silica matrix and nucleic acid/matrix complex from the second solution in step (h), wherein the external force is selected from the group consisting of centrifugation, filtration at atmospheric pressure, magnetic force, and vacuum filtration.

17. The method of claim 9, wherein the target nucleic acid is eluted from the nucleic acid/matrix complex using an elution buffer which is substantially free of chaotropic agents and which contains less than 200 mM salt concentration.

18. A method of reducing the concentration of endotoxins in a solution containing plasmid DNA and endotoxins, comprising:

a. providing a first silica matrix consisting essentially of silica, wherein the first silica matrix is equilibrated with a first equilibration buffer, wherein the equilibration buffer is substantially free of chaotropic agents;

b. providing a first solution comprising a plasmid DNA and endotoxins, wherein the first solution is substantially free of chaotropic agents;

c. combining the first silica matrix and the first solution, wherein at least one of the endotoxins forms an endotoxin/matrix complex with the first silica matrix, thereby producing a second solution which contains fewer of the endotoxins than are present in the first solution; and d. separating a second solution from the endotoxin/matrix complex.

19. The method of claim 18, wherein the first silica matrix consists essentially of a silica material selected from the group consisting of diatomaceous earth, ground glass, controlled pore glass, and silica gel.

20. The method of claim 18, wherein the first silica matrix is a silica magnetic particle.

21. The method of claim 18, wherein an external force selected from the group consisting of centrifugation, filtration at atmospheric pressure, and vacuum filtration is used in step (d) to separate the endotoxin/matrix complex from the second solution.

22. The method of claim 18, wherein at least 90% of the plasmid DNA present in the first solution is present in the second solution after the first silica matrix is removed therefrom.

23. The method of claim 18, further comprising the steps of:

providing a second silica matrix equilibrated with a second equilibration buffer;

combining the second solution with a second silica matrix in the presence of a plasmid DNA binding agent to form a binding solution, wherein the plasmid DNA forms a DNA/matrix complex with the second silica matrix;

separating the second silica matrix and DNA/matrix complex from the second solution; and eluting the nucleic acid from the DNA/matrix complex.

24. The method of claim 23, wherein the second silica matrix comprises a silica material selected from the group consisting of diatomaceous earth, ground glass, controlled pore glass, and silica gel.

25. The method of claim 23, wherein the second silica matrix is a silica magnetic particle.

26. The method of claim 23, wherein the second equilibration buffer comprises a chaotropic agent concentration of at least about 200 mM.

27. The method of claim 23, wherein the binding agent is a chaotropic agent, and the binding solution contains at least 1 M concentration of the chaotropic agent.

28. The method of claim 27, wherein the chaotropic agent is guanidine hydrochloride.

29. The method of claim 23, wherein the plasmid DNA is eluted from the DNA/matrix complex by adding an elution buffer to the DNA/matrix complex and second silica matrix, wherein the elution buffer is substantially free of chaotropic agents.

30. The method of claim 29, wherein the elution buffer contains no more than 200 mM of a non-chaotropic salt, and a chelating agent.

* * * * *